United States Patent [19]

Bonnefoy-Claudet et al.

[11] Patent Number: 4,882,680

[45] Date of Patent: Nov. 21, 1989

[54] PROCESS AND DEVICE FOR TAKING INTO ACCOUNT LOCATING PULSES SUPPLIED BY A GAMMA CAMERA

[75] Inventors: Jean-Paul Bonnefoy-Claudet, Grenoble; Corinne Mestais, Le Prieure Bernin, both of France

[73] Assignee: Commissariat a L'Energie Atomique, Paris, France

[21] Appl. No.: 199,102

[22] Filed: May 26, 1988

[30] Foreign Application Priority Data

May 27, 1987 [FR] France .................. 87 07479

[51] Int. Cl.$^4$ .................. G01T 1/164; G01T 1/208
[52] U.S. Cl. .................. 364/413.24; 250/369; 250/363.02
[58] Field of Search .............. 364/413.24; 250/363 S, 250/369

[56] References Cited

U.S. PATENT DOCUMENTS 4,629,894 12/1986 Lelong .................. 250/369 X
4,629,895 12/1986 Mestais et al. .................. 250/369
4,672,542 6/1987 Roux et al. .................. 250/369 X

FOREIGN PATENT DOCUMENTS 0131478 1/1985 European Pat. Off. .
2546632 11/1984 France .

Primary Examiner—Clark A. Jablon
Attorney, Agent, or Firm—Michael N. Meller

[57] ABSTRACT

To take account of the decrease time constant of the intensity of the light scintillation and the statistical fluctuation of the scintillation, which is a resolution deterioration factor, it is appropriate to integrate the electric pulse resulting from the detection of an event by photomultiplier tubes. If, during this integration, a stacking phenomenon occurs, a second pulse is superimposed on the first and falsifies the calculation of the scintillation coordinates. This stacking is eliminated by validating the calculation of these coordinates by checking the value reached by the scintillation energy at the end of said integration. The value of this energy is measured by integrating the signal representing the intensity of the light scintillation.

13 Claims, 3 Drawing Sheets

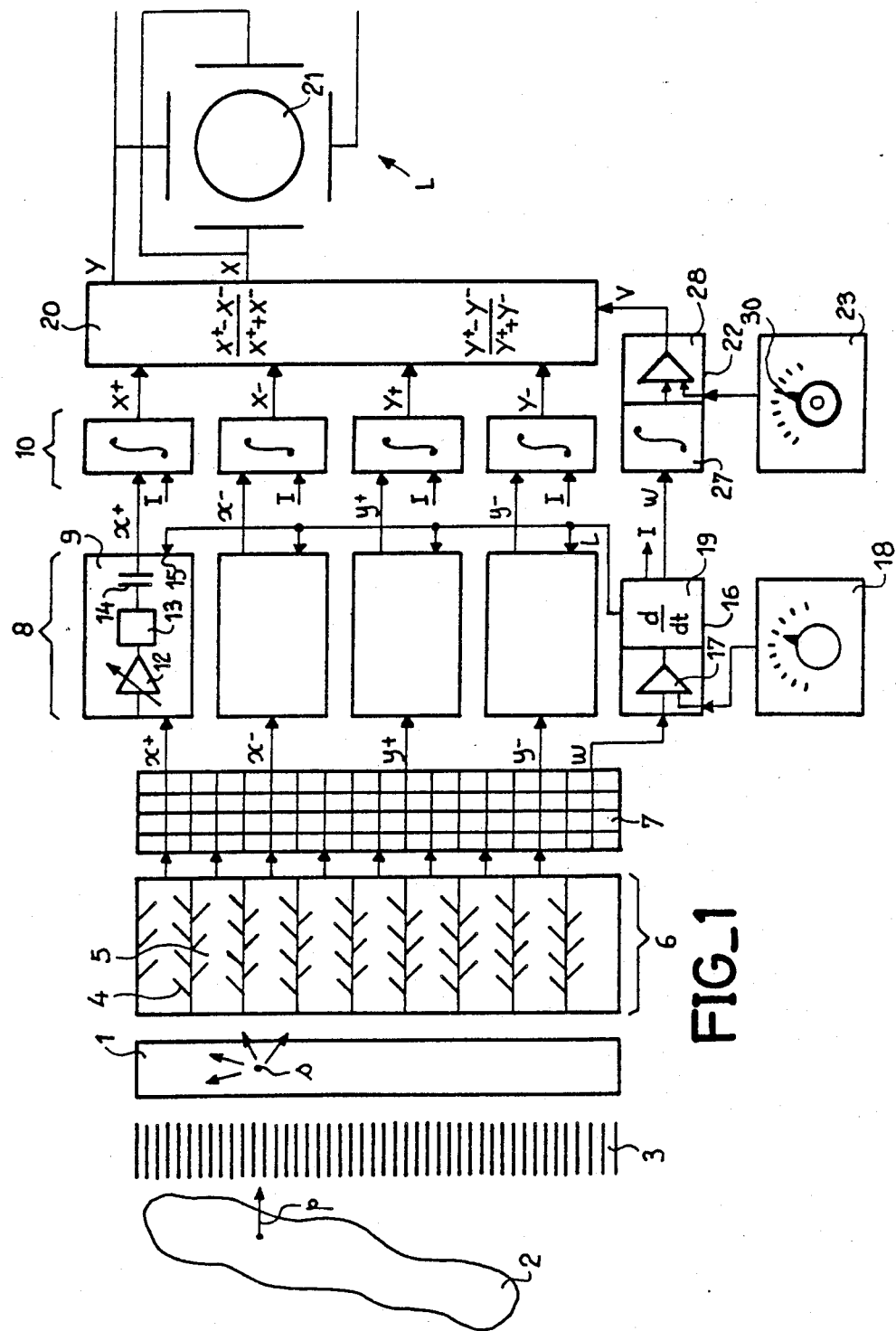
FIG_1

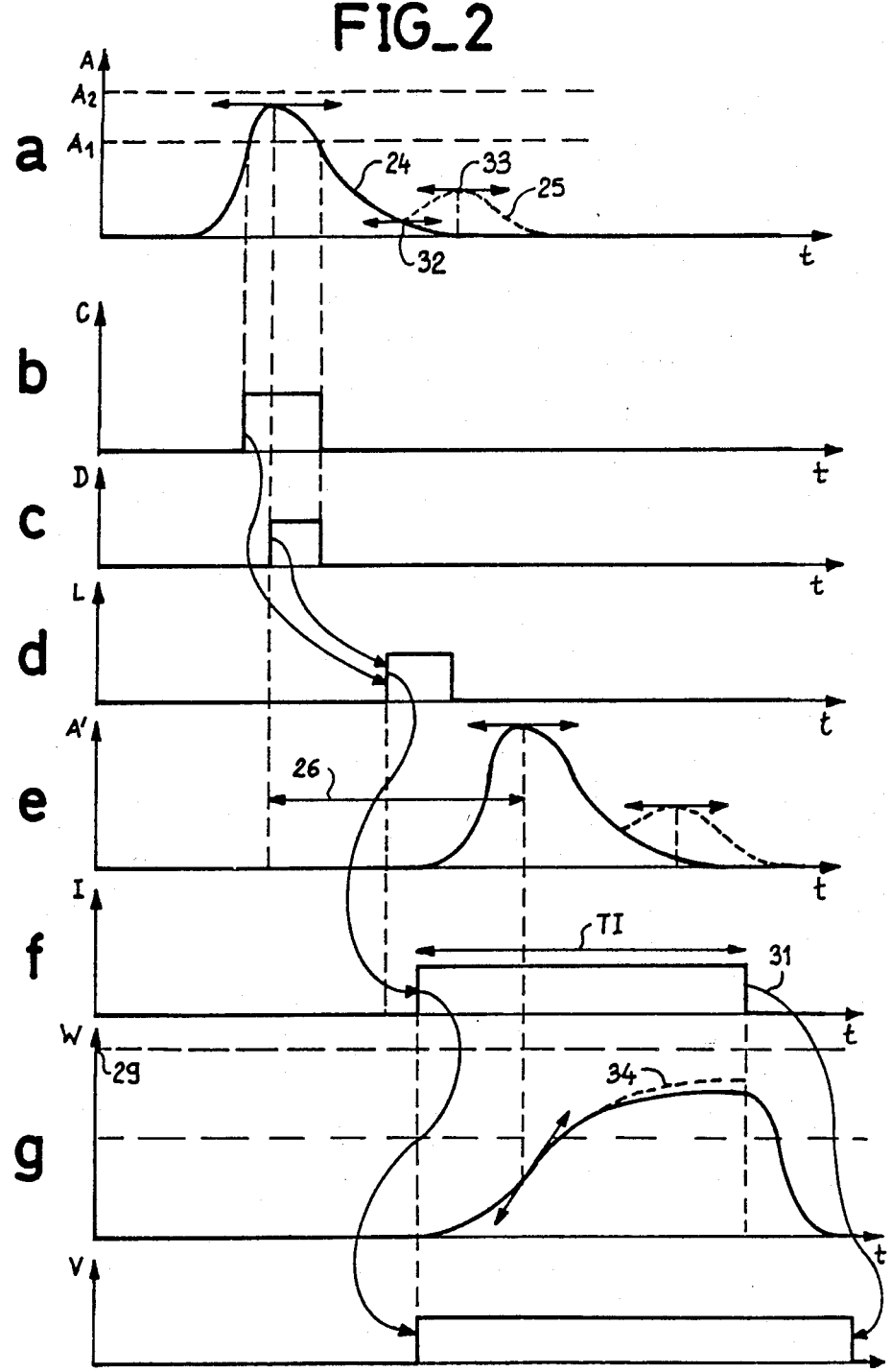
FIG_2

FIG_3
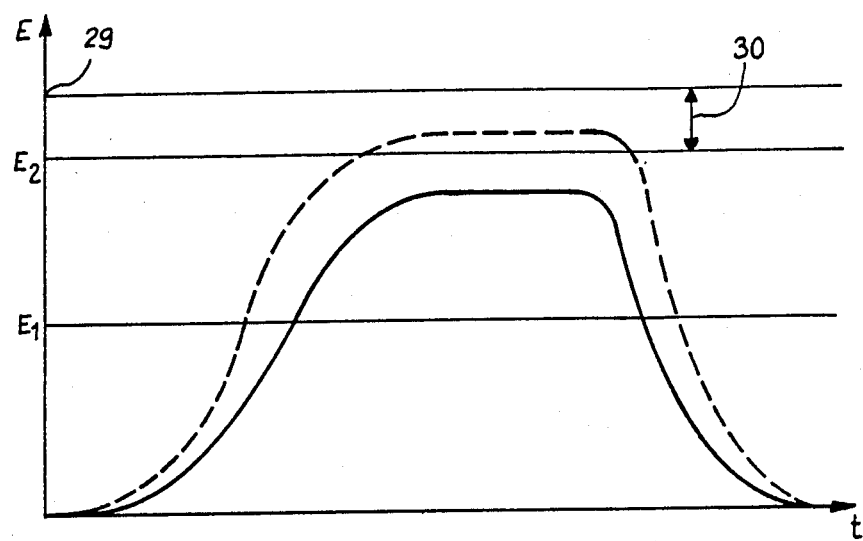

PROCESS AND DEVICE FOR TAKING INTO ACCOUNT LOCATING PULSES SUPPLIED BY A GAMMA CAMERA

The present invention relates to a process for taking account of locating pulses supplied by a gamma camera. It is more particularly used in the medical field, where gamma cameras are employed for producing images of organs to be examined for the purpose of making a diagnosis. It relates to scintillation or gamma cameras of the Anger type and whereof U.S. Pat. No. 3,011,057 describes the operating principles and production. These gamma cameras are used for detecting and visually displaying photons emitted by radioactive bodies.

Gamma cameras are used in nuclear medicine for rendering visible in an organ the distribution of the molecules labelled by a radioactive isotope injected into a patient. A gamma camera generally comprises a collimator for focusing the gamma photons emitted by the patient, a scintillation crystal for transforming the gamma photons into light photons or scintillations and a system of photomultiplier tubes transforming each of the scintillations into electric pulses, called electrical contributions of the tubes. A gamma camera also generally comprises electronic circuits for producing, on the basis of the electrical contributions supplied by the photomultiplier tubes, signals of coordinates X and Y of the location where the scintillation has occurred, as well as a validation signal Z, when the amplitude of the scintillation belongs to a predetermined energy band.

Each detection chain is followed by a display means generally incorporating a cathode ray oscilloscope controlled by the signals of coordinates X, Y and Z for visualizing by a light spot on the screen the impact point of the gamma photon on the crystal. The visual display means may optionally incorporate a photographic apparatus for forming an image of the observed organ, whilst integrating a large number of light spots produced on the cathode ray screen. It may also include a device for digitally processing the images and the latter can in particular be used for reconstructing sectional images of the examined organs, in order to produce tomographs thereof. In the latter case, image reconstruction algorithms identical to those employed in tomodensitometry are used.

Among other qualities a gamma camera must have a good spatial resolution, i.e. the capacity to distinguish small closely juxtaposed radioactive sources, a good counting rate response, i.e. the capacity to process a large number of events per time unit and an image quality which is independant of the energy of the isotope in question. The spatial resolution is dependant on the accuracy of calculating the coordinates X and Y. The quality of producing these coordinates is essentially dependant on physical laws governing the operation of the different parts of the gamma camera. Thus, the interaction of a gamma photon with the crystal gives rise to a light scintillation, whereof the intensity decreases exponentially with time. The time constant of this decrease is a characteristic of the scintillation crystal used. For a thallium-activated sodium iodide crystal, NaI (T1), it is approximately 250 nanoseconds. This scintillation is seen by several photomultiplier tubes simultaneously. The light photons forming said scintillation remove photoelectrons from the photocathodes of the photomultiplier tubes. The number of photoelectrons removed obeys, for a given scintillation, the statistical Poisson law. This means that the electrical contribution of a photomultiplier tube receiving a scintillation has an amplitude, whereof the value follows a statistical Poisson distribution. The mean value of this amplitude is a function of the energy of the incident light photons.

As a scintillation is seen by several photomultiplier tubes simultaneously, the determination of the location of said scintillation on the crystal, which itself represents the emission point of the exciting gamma photon is obtained by calculating the location of the barycentre of the electrical contribution supplied by the group of photomultiplier tubes excited by said scintillation. According to Anger, this calculation takes place in simple manner by injecting electrical contributions through a set of resistor arrays. The resistance values of the arrays are a function, for so-called locating arrays, of the positions of the photomultiplier tubes to which they are connected. The positions of these tubes are referenced with respect to Cartesian reference axes, whereof the intersection point is generally in the center of the group of tubes.

The most difficult problem to solve, for a given scintillation, is to determine as accurately as possible the mean value of the amplitudes of each of the contributions. It is also known to time integrate these contributions over a period of approximately three times the decrease time constant of the scintillations of the scintillation crystal. The integration or counting time is dependant on the time constant of the crystal. The accuracy of the measurement suffers from errors due to the statistical Poisson fluctuation. Thus, the standard variation of the fluctuation of the amplitude of the contributions according to Poisson statistics is inversely proportional to the square root of the number of photoelectrons removed. Thus, the longer the integration, the greater the number of photoelectrons taken into account and the smaller the standard variation and consequently the more the mean value of this contribution is accurately evaluated.

Thus, as the operation of calculating the location of the barycentre is a linear operation, it is more economic to perform the integration at the outlet of each of the arrays of resistors of the array set. These arrays only carry out one weighting of the contributions as a function of the location of the tubes on the crystal. The electric pulses supplied at the outlet of the set of resistor arrays are said to be weighted pulses. The counting time is directly linked with the quality of spatial resolution of the gamma camera and this quality is obtained to the detriment of the counting rate, i.e. to the detriment of the number of events per second taken into account.

Certain problems are encountered in the integration operation. Such a gamma camera was described in French Patent Application No. 83.08824, filed on May 27th, 1983. Apart from all the electronic circuits used for locating the scintillations, it has validation circuits for taking account of the scintillations, whose amplitude is in a predetermined range and which are not followed, after the integration time, by the untimely arrival of another scintillation, possibly even produced at another location on the crystal and whose intervention may falsify the calculation of the location. The determination of the presence of a scintillation takes place therein by comparing the amplitude of a time signal, called an energy signal, with a threshold constituting one of the two limits of the predetermined range. Apart from the comparison of the energy signal with a threshold, a study takes place of the zero passage of the derivative relative to the time of said signal. The thus undertaken differentiation, during said zero passage, marks the culminating point of a weighted pulse forming said signal and representing the energy. If this peak is produced after the clearing of the bottom threshold of the range and if the top threshold of the range is not cleared, it is deduced therefrom that the scintillation is to be taken into account.

When a so-called stacking phenomenon occurs, a second scintillation is formed before the effects of the first scintillation have completely vanished. In the aforementioned patent application a logic circuit is provided for preventing the taking into account of said second scintillation if it is produced at the end of too short a time following the appearance of the first. However, nothing is provided for rejecting the taking into account of the scintillation which has just been measured if, during the integration time thereof, another scintillation is produced. A device is known which makes it possible to achieve this result. It consists of using the same logic circuit as that used for determining the presence of a scintillation for the time necessary for the integration of said scintillation. If this logic circuit notes the presence of a second peak, it is possible to abandon the measurement performed and not to take account of its significance.

However, the latter method suffers from a disadvantage. Thus, it does not give a coherent result in the measurement where a scintillation is always followed by scintillation interference which, during the signal decrease time, produce interference peaks, whose detection leads to the rejection of the measurement of the scintillation performed. Therefore if such a circuit functions perfectly bearing in mind the scintillation noise, the counting rate of the gamma camera becomes zero and all the strokes or pulses are rejected because they suffer from noise. It is wished for the logics circuit to take account of a threshold value a virtually insurmountable difficulty is encountered, due to the fact that the time signal of the scintillation decreases during the integration period. It then becomes difficult to compare with a given threshold a signal resulting from the sum of the expected decrease of the scintillation signal and a random unwanted signal to be detected. Thus, in the state of the art, it is necessary to ignore the appearance of stacks. Moreover, when the latter occur they disturb the location signal. Therefore this problem requires solving in order to improve the spatial resolution of the image.

The present invention therefore aims at obviating these disadvantages by proposing a process for taking into account in which no attention is paid to the value of the time signal representing the energy or of the derivative of said signal, account instead being taken of its integration during a predetermined time. Preferably, this predetermined time is equal to the integration time used for calculating the location pulses. It then becomes possible, following said integration, to define a range of the scintillation energy value in which the calculated location pulses are to be taken into account. Thus, with respect to a spectrometry window characteristic of the isotope used, it is possible to define another spectrometry window, whereof the bottom threshold is maintained and wherein the top threshold is positively displaced by a certain value so as to take account of the scintillations suffering from noise and so as not to bring about an excessive deterioration of the camera counting rate. Moreover, by regulating the admissible proportion by which the scintillation energy can exceed the spectrometry window, it is possible to regulate the stacking tolerance which is accepted. This is not possible with any of the known systems.

The present invention therefore relates to a process for taking account of the locating pulses supplied by a gamma camera, in which:

scintillations produced by gamma radiation in a scintillation crystal are detected and amplified by a system of photomultiplier tubes in order to constitute electrical contributions of said tubes, the electrical contributions are successively weighted in the resistor arrays, transmitted by transmission circuits if the maximum scintillation amplitude belongs to a predetermined range and then integrated in integrators for producing integrated pulses, the integrated pulses are processed for producing said locating pulses, characterized in that the taking into account is validated if the energy of the scintillation belongs to a predetermined energy band.

The invention is described in greater detail hereinafter relative to non-limitative embodiments and the attached drawings, wherein show:

FIG. 1 shows an apparatus for performing the process of the invention.

FIGS. 2a to 2g shows time charts of signals occuring in the inventive process.

FIGS. 3 shows the statistical representation of a displaced spectrometry window used for constituting a stacking tolerance range according to the invention.

FIG. 1 shows a gamma camera for performing the process of the invention. This gamma camera essentially comprises a scintillator 1 for receiving gamma photons p emitted by a radioactive body 2, optionally after they have been focussed by a collimator 3. Scintillations s are emitted in the form of light photons, which excite the dynodes 4 of the photomultiplier tubes 5 of a group 6 of photomultiplier tubes positioned facing the said scintillator. The scintillations are then transformed by each of the tubes into electrical tube contributions. Each of the latter is introduced into a set 7 of resistor arrays, which process weighted pulses. In a conventional gamma camera, there are five resistor arrays for supplying weighted pulses respectively $x^+$, $x^-$, $y^+$, $y^-$ and w. The four first represent the location of the point of the scintillation s on the crystal 1, whilst the fifth w represents the amplitude of the scintillation. The latter is often called the energy of the scintillation and it only has said energy if the said signal is time integrated.

A group 8 of transmission circuits, like circuit 9, ensures the transmission of the weighted pulses to an array 10 of integrators, such as 11. The transmission circuits essentially have in each case a variable gain amplifier 12, a delay line 13 and a basic potential restoration circuit 14. These features of transmission circuits 9 correspond to a preferred embodiment, but do not form part of the present invention. The usefulness of transmission circuit 9 is that they can be controlled by a control input 15, which receives a logic instruction L from a circuit 16 for detecting the presence of a scintillation.

This system functions in the following way. The circuits 16 which receives the signal w representing the scintillation energy, supplies the instruction L for validating the operation of the transmission circuits 9 when a threshold comparator 17 detects that the signal w exceeds a predetermined threshold, which is fixed by a display device 18 and when a differentiation circuit 19 detects, subsequently to the clearing of the threshold, the presence of a peak of the energy-representing signal. Delay line 13 authorizes the restoration of the basic potential by circuit 14, in response to instruction L, before said weighted pulse is transmitted to an integrator of the integrator array 10. The weighted and transmitted pulses are then integrated in the integrators, which respectively supply at their output the integrated locating pulses $X^+$, $X^-$, $Y^+$ and $Y^-$. A known processing circuit 20 then processes the actual locating pulses, which are then applied to the deflecting plates of a cathode ray oscillograph 21, whilst the logic instruction L is applied to the Wehnelt electrode of said oscillograph in order to bring about the appearance of an impact on its screen.

What characterizes the invention is the realisation of a circuit 22 for measuring the energy of the scintillation and for comparing said energy with a predetermined energy band. The latter can be indicated by a display device 23. FIGS. 2a to 2h and FIG. 3 make it possible to better understand the invention. FIG. 2a is a time chart of the amplitude of a scintillation 24 followed by interference 25, which deteriorates its significance. The determination that the scintillation belongs to a spectrometry window E1–E2 (FIG. 3) is likened to the fact that the maximum amplitude of the weighted signal w representing said energy belongs to a predetermined range A1–A2. When the amplitude of signal w temporarily exceeds the lower threshold A1 of the range, comparator 17 emits an instruction C (FIG. 2b). When subsequently the signal w culminates in the range A1–A2, differenciator 18 emits an instruction D (FIG. 2c). Instruction C and D are then used in a logic circuit contained in circuit 16 for producing an instruction L (FIG. 2d) for validating the transmission of the weighted pulses.

Instruction L, which is slightly delayed to take account of the basic potential restoration operation, becomes an instruction I (FIG. 2f) applied to the integrators of array 10. The integrators, such as 11 then integrate the weighted and transmitted pulses reaching them after a delay 26 imposed by delay line 13 (FIG. 2e). In known manner, the integration time TI of integrators 11 is predetermined and is equal to a multiple of the decrease time of the scintillation signal. This integration time is generally equal to three times this decrease constant. Throughout the duration of this integration, the integrators associated with the transmitted pulses representing the location integrate the signal reaching them. In the same way, an integrator 27 contained in circuit 22 integrates signal w and transforms it into a truly representative signal W at the end of said integration of the energy of the scintillation taken into account.

Signal W is then introduced into a comparator 28, where it is compared with a threshold 29 processed by display 23 (FIG. 2g). Threshold 29 exceeds threshold E2 of the investigated energy band (FIG. 3) by a value 30 indicated by the display. At the output, comparator 28 issues an instruction V, e.g. in the form of a pulse passing into the active state at the time of applying instruction L.

The pulse representing the instruction V is either deactivated at the end of integration or even after said integration (arrow 31, FIGS. 2f–2h), or deactivated as a function of the exceeding of threshold 29 by energy signal W. Instruction V lasts a little longer than the integration instruction I in order to authorise, at the end of said integration, the processing of the integrated location pulses in the location pulse processing circuit. However, if the signal of energy W has cleared threshold 29, comparator 28 supplies a deactivation signal for V prior to the transmission of integrated location pulses, so that the processing by circuit 20 is prevented.

In the state of the art, the presence of the interference scintillation 25 was detected, with the aforementioned disadvantages, by the zero passage of the differentiated signal resulting from the start of the appearance 32 of said interference, or the maximum 33 of said interference (FIG. 2a). In the invention the interference 25 causes a displacement 34 of the signal representing the scintillation energy. If this displacement is small taking into account is authorized but is prevented in the opposite case. It is pointed out that the invention offers a possibility of regulating the stacking tolerance. No regulating possibility can be considered on using a detection of the zero passage of the differentiated, signal, the interference 25 definitely being taken into account (for invalidation) no matter what its significance.

A preferred embodiment has been described, but it is possible to reduce the number of arrays in the set of arrays by using in place of the weighted pulse w, the sum of the weighted pulses $x^+$, $x^-$, $y^+$ and $y^-$. To the extent that the sum of these weighted pulses makes it possible to evaluate the amplitude of the scintillation, the presence of the so-called energy array becomes unimportant.

We claim:

1. A process for taking into account locating pulses supplied by a gamma camera comprising the following steps:
    producing scintillations in a scintillation crystal in response to gamma camera radiation,
    amplifying said scintillations by means of a plurality of photomultiplier tubes to develop electrical contributions of said tubes,
    weighting said electrical contributions successively in resistor arrays,
    transmitting said weighted electrical contributions by means of transmission circuits if the maximum amplitude of said scintillations is in a predetermined range,
    integrating said weighted and transmitted electrical contributions in integrators to produce integrated pulses,
    processing said integrated pulses for producing said locating pulses, and
    measuring the energy of said scintillations and validating the taking into account of said locating pulses when the energy of said scintillations belongs in a predetermined energy band.

2. A process according to claim 1 wherein the step of measuring the energy of said scintillations consists of integrating the amplitude of said scintillations.

3. A process according to claim 2 wherein the integration time of said weighted and transmitted electrical contributions.

4. A process according to claim 3 wherein said predetermined energy band is regulated as a function of a predetermined stacking tolerance of said scintillations.

5. A process according to claim 2 wherein said predetermined energy band is regulated as a function of a predetermined stacking tolerance of said scintillations.

6. A process according to claim 2 wherein the measurement by integration of the amplitude of said scintillations is evaluated by the sum of the locating pulses.

7. A process according to claim 1 wherein said predetermined energy band is regulated as a function of a predetermined stacking tolerance of said scintillations.

8. A process according to claim 1 wherein the validation of the taking into account of said locating pulses includes the step of comparing the energy value of said scintillations to a threshold.

9. A process according to claim 1 wherein said step of transmitting said electrical contributions includes a time delay, the step of restoring a basic potential and the step of transmitting an authorization signal.

10. A process according to claim 9 wherein the step of transmitting said authorization signal includes the step of comparison with a threshold associated with a peak detection.

11. A process according to claim 10 wherein said peak detection includes steps of differentiation and a zero comparison.

12. Apparatus for taking into account locating pulses supplied by a gamma camera comprising:
- a scintillation crystal for receiving gamma radiation and for producing scintillations,
- a group of photomultiplier tubes responsive to said scintillations for detecting and amplifying said scintillations to produce electrical contributions,
- weighting means coupled to the outputs of said photomultiplier tubes for supplying weighted electrical contributions,
- transmission circuits coupled to the output of said weighting means for amplifying and transmitting said weighted electrical contributions,
- integrators coupled to the outputs of said transmissions circuits for integrating said weighted and amplified electrical contributions and producing integrated signals,
- measuring means for measuring the energy of said scintillations, said measuring means being coupled to an output of said photomultiplier tubes, to inputs of said transmission circuits and to an input of an integrator, and
- comparison means coupled to the output of said integrator for supplying a validation signal for validating the taking into account of said locating pulses when the measurement of said energy of said scintillations belongs to a predetermined energy band.

13. Apparatus according to claim 12 wherein said measuring means comprises a threshold comparator followed by a differentiator and said comparison means comprises an integrator followed by a threshold comparator.

* * * * *